(12) United States Patent
Schroeder et al.

(10) Patent No.: US 9,421,104 B2
(45) Date of Patent: Aug. 23, 2016

(54) ANTIOXIDANT DOPING OF CROSSLINKED POLYMERS TO FORM NON-ELUTING BEARING COMPONENTS

(71) Applicant: Biomet Manufacturing, LLC, Warsaw, IN (US)

(72) Inventors: David W. Schroeder, Winona Lake, IN (US); Jordan H. Freedman, Fort Wayne, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 277 days.

(21) Appl. No.: 14/171,237

(22) Filed: Feb. 3, 2014

(65) Prior Publication Data

US 2014/0148911 A1    May 29, 2014

Related U.S. Application Data

(62) Division of application No. 12/179,274, filed on Jul. 24, 2008, now Pat. No. 8,641,959.

(60) Provisional application No. 60/952,452, filed on Jul. 27, 2007.

(51) Int. Cl.
*C08K 5/15* (2006.01)
*A61F 2/34* (2006.01)
(Continued)

(52) U.S. Cl.
CPC . *A61F 2/34* (2013.01); *A61F 2/389* (2013.01); *A61L 27/16* (2013.01); *B23P 15/003* (2013.01);
(Continued)

(58) Field of Classification Search
CPC ............ A61F 2/34; A61F 2/389; A61F 2/32; A61F 2/38; B23P 15/003; B29C 71/02; B29C 71/04; B29C 2071/022; B29C 2035/085; A61L 27/16; B29L 2031/7532
See application file for complete search history.

(56) References Cited

U.S. PATENT DOCUMENTS 2,948,666 A    8/1960    Lawton
3,362,897 A    1/1968    Lawton
(Continued)

FOREIGN PATENT DOCUMENTS

CA    1257745 A    7/1989
DE    19914571 A1    1/2001
(Continued)

OTHER PUBLICATIONS

"U.S. Appl. No. 12/179,274, Advisory Action mailed Nov. 8, 2011", 6 pgs.
(Continued)

*Primary Examiner* — Galen Hauth
(74) *Attorney, Agent, or Firm* — Schwegman Lundberg & Woessner, P.A.

(57) ABSTRACT

Methods provide a non-eluting antioxidant doped UHMWPE in the form of an implant bearing component. The process includes the steps of: (a) providing a preform; (b) irradiating the preform with γ-irradiation to crosslink the UHMWPE; (c) doping the crosslinked preform by exposing it to an antioxidant composition at a temperature below the melting point of the UHMWPE; (d) removing the doped material from contact with the antioxidant composition; and then (e) annealing by heating the doped material at a temperature above 30° C. and below the melting point of the UHMWPE; followed by (f) making an implant bearing component from the doped material, wherein at least 1 mm but no more than about 15 mm of material are removed to make the component.

18 Claims, 3 Drawing Sheets

(51) Int. Cl.
*A61L 27/16* (2006.01)
*B29C 71/02* (2006.01)
*B29C 71/04* (2006.01)
*B23P 15/00* (2006.01)
*A61F 2/32* (2006.01)
*A61F 2/38* (2006.01)
*B29C 35/08* (2006.01)
*B29L 31/00* (2006.01)

(52) U.S. Cl.
CPC ............... B29C 71/02 (2013.01); B29C 71/04 (2013.01); *A61F 2/32* (2013.01); *A61F 2/38* (2013.01); *B29C 2035/085* (2013.01); *B29C 2071/022* (2013.01); *B29L 2031/7532* (2013.01)

(56) References Cited

U.S. PATENT DOCUMENTS

| | | |
|---|---|---|
| 3,563,870 A | 2/1971 | Tung et al. |
| 3,886,056 A | 5/1975 | Kitamaru et al. |
| 3,956,253 A | 5/1976 | Braun |
| 4,055,862 A | 11/1977 | Farling |
| 4,171,338 A | 10/1979 | Mason et al. |
| 4,224,696 A | 9/1980 | Murray et al. |
| 4,265,959 A | 5/1981 | Sano et al. |
| 4,281,420 A | 8/1981 | Raab et al. |
| 4,348,350 A | 9/1982 | Meier et al. |
| 4,390,666 A | 6/1983 | Moriguchi et al. |
| 4,582,656 A | 4/1986 | Hoffmann et al. |
| 4,586,995 A | 5/1986 | Randall et al. |
| 4,587,163 A | 5/1986 | Zachariades |
| 4,636,340 A | 1/1987 | Itaba et al. |
| 4,655,769 A | 4/1987 | Zachariades |
| 4,668,577 A | 5/1987 | Ohta et al. |
| 4,747,990 A | 5/1988 | Gaussens et al. |
| 4,778,633 A | 10/1988 | Kiang et al. |
| 4,820,466 A | 4/1989 | Zachariades |
| 4,857,247 A | 8/1989 | Raczkowski |
| 4,902,460 A | 2/1990 | Yagi et al. |
| 4,938,913 A | 7/1990 | Ward et al. |
| 5,030,402 A | 7/1991 | Zachariades |
| 5,030,487 A | 7/1991 | Rosenzweig |
| 5,037,928 A | 8/1991 | Li et al. |
| 5,066,755 A | 11/1991 | Lemstra |
| 5,096,654 A | 3/1992 | Craggs et al. |
| 5,130,376 A | 7/1992 | Shih |
| 5,160,464 A | 11/1992 | Ward et al. |
| 5,169,589 A | 12/1992 | Francoeur et al. |
| 5,200,129 A | 4/1993 | Kobayashi et al. |
| 5,200,439 A | 4/1993 | Asanuma |
| 5,204,045 A | 4/1993 | Courval et al. |
| 5,210,130 A | 5/1993 | Howard, Jr. |
| 5,234,652 A | 8/1993 | Woodhams et al. |
| 5,266,246 A | 11/1993 | Johnson et al. |
| 5,276,079 A | 1/1994 | Duan et al. |
| 5,358,529 A | 10/1994 | Davidson |
| 5,405,393 A | 4/1995 | Falkenstrom |
| 5,407,623 A | 4/1995 | Zachariades et al. |
| 5,414,049 A | 5/1995 | Sun et al. |
| 5,428,079 A | 6/1995 | Bastiaansen et al. |
| 5,439,949 A | 8/1995 | Lucas et al. |
| 5,449,745 A | 9/1995 | Sun et al. |
| 5,466,530 A | 11/1995 | England et al. |
| 5,478,906 A | 12/1995 | Howard, Jr. |
| 5,543,471 A | 8/1996 | Sun et al. |
| 5,552,104 A | 9/1996 | Denicola, Jr. et al. |
| 5,577,368 A | 11/1996 | Hamilton et al. |
| 5,650,485 A | 7/1997 | Sun et al. |
| 5,684,124 A | 11/1997 | Howard, Jr. et al. |
| 5,709,020 A | 1/1998 | Pienkowski et al. |
| 5,728,748 A | 3/1998 | Sun et al. |
| 5,824,411 A | 10/1998 | Shalaby et al. |
| 5,827,904 A | 10/1998 | Hahn |
| 5,830,396 A | 11/1998 | Higgins et al. |
| 5,879,400 A | 3/1999 | Merrill et al. |
| 6,017,975 A | 1/2000 | Saum et al. |
| 6,048,480 A | 4/2000 | Doyle |
| 6,051,487 A | 4/2000 | Gardner et al. |
| 6,143,232 A | 11/2000 | Rohr |
| 6,146,426 A | 11/2000 | Doyle |
| 6,165,220 A | 12/2000 | McKellop et al. |
| 6,168,626 B1 | 1/2001 | Hyon et al. |
| 6,174,934 B1 | 1/2001 | Sun et al. |
| 6,184,265 B1 | 2/2001 | Hamilton et al. |
| 6,228,900 B1 | 5/2001 | Shen et al. |
| 6,242,507 B1 | 6/2001 | Saum et al. |
| 6,245,276 B1 | 6/2001 | McNulty et al. |
| 6,281,264 B1 | 8/2001 | Salovey et al. |
| 6,316,158 B1 | 11/2001 | Saum et al. |
| 6,355,215 B1 | 3/2002 | Poggie et al. |
| 6,365,089 B1 | 4/2002 | Krebs et al. |
| 6,372,814 B1 | 4/2002 | Sun et al. |
| 6,395,799 B1 | 5/2002 | Johnson |
| 6,432,349 B1 | 8/2002 | Pletcher et al. |
| 6,448,315 B1 * | 9/2002 | Lidgren ............... A61L 27/16 524/110 |
| 6,458,727 B1 | 10/2002 | Jones et al. |
| 6,464,926 B1 | 10/2002 | Merrill et al. |
| 6,494,917 B1 | 12/2002 | McKellop et al. |
| 6,503,439 B1 | 1/2003 | Burstein |
| 6,547,828 B2 | 4/2003 | Scott et al. |
| 6,562,540 B2 | 5/2003 | Saum et al. |
| 6,641,617 B1 | 11/2003 | Merrill et al. |
| 6,664,308 B2 | 12/2003 | Sun et al. |
| 6,686,437 B2 | 2/2004 | Buchman et al. |
| 6,692,679 B1 | 2/2004 | McNulty et al. |
| 6,709,464 B2 | 3/2004 | Scott et al. |
| 6,726,727 B2 | 4/2004 | Scott et al. |
| 6,786,933 B2 | 9/2004 | Merrill et al. |
| 6,800,670 B2 | 10/2004 | Shen et al. |
| 6,818,020 B2 | 11/2004 | Sun et al. |
| 6,818,172 B2 | 11/2004 | King et al. |
| 6,852,772 B2 | 2/2005 | Muratoglu et al. |
| 6,905,511 B2 | 6/2005 | Wang et al. |
| 7,214,764 B2 | 5/2007 | King |
| 7,268,039 B2 | 9/2007 | Fishburn et al. |
| 7,344,672 B2 | 3/2008 | Schroeder et al. |
| 7,431,874 B2 | 10/2008 | Muratoglu et al. |
| 7,462,318 B2 | 12/2008 | Schroeder et al. |
| 7,498,365 B2 | 3/2009 | Muratoglu et al. |
| 7,517,919 B2 | 4/2009 | Wang et al. |
| 7,547,405 B2 | 6/2009 | Schroeder et al. |
| 7,635,725 B2 | 12/2009 | Bellare et al. |
| 7,780,896 B2 | 8/2010 | Schroeder et al. |
| 8,641,959 B2 | 2/2014 | Schroeder et al. |
| 2001/0049401 A1 | 12/2001 | Salovey et al. |
| 2002/0007219 A1 | 1/2002 | Merrill et al. |
| 2002/0037944 A1 | 3/2002 | Shen et al. |
| 2002/0125614 A1 | 9/2002 | King et al. |
| 2002/0156536 A1 | 10/2002 | Harris et al. |
| 2003/0013781 A1 | 1/2003 | Merrill et al. |
| 2003/0045603 A1 | 3/2003 | Salovey et al. |
| 2003/0105182 A1 | 6/2003 | Merrill et al. |
| 2003/0119935 A1 | 6/2003 | Merrill et al. |
| 2003/0125513 A1 | 7/2003 | King |
| 2003/0137081 A1 | 7/2003 | Pitkanen |
| 2003/0139555 A1 | 7/2003 | Hubbard et al. |
| 2003/0144741 A1 | 7/2003 | King et al. |
| 2003/0158287 A1 | 8/2003 | Salovey et al. |
| 2003/0208278 A1 | 11/2003 | Richard |
| 2003/0212161 A1 | 11/2003 | McKellop et al. |
| 2003/0229155 A1 | 12/2003 | Wang et al. |
| 2004/0051213 A1 | 3/2004 | Muratoglu et al. |
| 2004/0132856 A1 | 7/2004 | Merrill et al. |
| 2004/0208841 A1 | 10/2004 | Salovey et al. |
| 2004/0265165 A1 | 12/2004 | King |
| 2004/0266902 A1 | 12/2004 | Shen et al. |
| 2005/0006821 A1 | 1/2005 | Merrill et al. |
| 2005/0010288 A1 | 1/2005 | Merrill et al. |
| 2005/0043431 A1 | 2/2005 | Wang et al. |
| 2005/0043815 A1 | 2/2005 | King et al. |
| 2005/0048096 A1 | 3/2005 | Shen et al. |
| 2005/0056971 A1 | 3/2005 | Merrill et al. |
| 2005/0059750 A1 | 3/2005 | Sun et al. |

(56) References Cited

U.S. PATENT DOCUMENTS

| | | |
|---|---|---|
| 2005/0069696 A1 | 3/2005 | King et al. |
| 2005/0096749 A1 | 5/2005 | Marrill et al. |
| 2005/0165495 A1 | 7/2005 | Merrill et al. |
| 2005/0194723 A1 | 9/2005 | Muratoglu et al. |
| 2006/0149387 A1 | 7/2006 | Smith et al. |
| 2006/0149388 A1 | 7/2006 | Smith et al. |
| 2006/0155383 A1 | 7/2006 | Smith et al. |
| 2006/0223905 A1 | 10/2006 | Mimnaugh et al. |
| 2006/0264541 A1 | 11/2006 | Lederer et al. |
| 2007/0059334 A1 | 3/2007 | Abt et al. |
| 2007/0114702 A1 | 5/2007 | Muratoglu et al. |
| 2007/0265369 A1 | 11/2007 | Muratoglu et al. |
| 2007/0267030 A1 | 11/2007 | Muratoglu et al. |
| 2007/0275030 A1 | 11/2007 | Muratoglu et al. |
| 2008/0036111 A1 | 2/2008 | Sun |
| 2008/0067724 A1 | 3/2008 | Muratoglu et al. |
| 2008/0090934 A1 | 4/2008 | Muratoglu et al. |
| 2008/0119582 A1 | 5/2008 | Muratoglu et al. |
| 2008/0140196 A1 | 6/2008 | Schroeder et al. |
| 2008/0214692 A1 | 9/2008 | Muratoglu et al. |
| 2008/0215142 A1 | 9/2008 | Muratoglu et al. |
| 2008/0274161 A1 | 11/2008 | Muratoglu et al. |
| 2009/0054545 A1 | 2/2009 | Muratoglu et al. |
| 2009/0224428 A1 | 9/2009 | Schroeder et al. |

FOREIGN PATENT DOCUMENTS

| | | |
|---|---|---|
| EP | 0729981 B1 | 3/2002 |
| EP | 1334993 A2 | 8/2003 |
| GB | 1281956 A | 7/1972 |
| JP | 526761 A | 7/1975 |
| JP | 57211347 A | 12/1982 |
| JP | 62216723 A | 9/1987 |
| JP | 62243634 A | 10/1987 |
| JP | 02175137 A | 7/1990 |
| JP | 04198201 A | 7/1992 |
| JP | 05507748 A | 11/1993 |
| JP | 08012771 A | 1/1996 |
| JP | 09122222 A | 5/1997 |
| JP | 09141729 A | 6/1997 |
| JP | 10166468 A | 6/1998 |
| JP | 1160791 A | 3/1999 |
| JP | 11077778 A | 3/1999 |
| JP | 11239611 A | 9/1999 |
| WO | WO-9310953 A1 | 6/1993 |
| WO | WO-9506148 A1 | 3/1995 |
| WO | WO-9801085 A1 | 1/1998 |
| WO | WO-9814223 A1 | 4/1998 |
| WO | WO-03049930 A | 6/2003 |

OTHER PUBLICATIONS

"U.S. Appl. No. 12/179,274, Examiner Interview Summary mailed May 5, 2011", 3 pgs.

"U.S. Appl. No. 12/179,274, Examiner Interview Summary mailed Dec. 11, 2012", 3 pgs.

"U.S. Appl. No. 12/179,274, Final Office Action mailed Jul. 21, 2011", 15 pgs.

"U.S. Appl. No. 12/179,274, Final Office Action mailed Jul. 26, 2013", 7 pgs.

"U.S. Appl. No. 12/179,274, Final Office Action mailed Oct. 22, 2012", 16 pgs.

"U.S. Appl. No. 12/179,274, Non Final Office Action mailed Jan. 14, 2013", 17 pgs.

"U.S. Appl. No. 12/179,274, Non Final Office Action mailed Apr. 25, 2012", 16 pgs.

"U.S. Appl. No. 12/179,274, Non Final Office Action mailed Dec. 9, 2010", 13 pgs.

"U.S. Appl. No. 12/179,274, Notice of Allowance mailed Oct. 2, 2013", 10 pgs.

"U.S. Appl. No. 12/179,274, Response filed Apr. 11, 2013 to Non Final Office Action mailed Jan. 14, 2013", 11 pgs.

"U.S. Appl. No. 12/179,274, Response filed May 9, 2011 to Non Final Office Action mailed Dec. 9, 2010", 13 pgs.

"U.S. Appl. No. 12/179,274, Response filed Jul. 25, 2012 to Non Final Office Action mailed Apr. 25, 2012", 16 pgs.

"U.S. Appl. No. 12/179,274, Response filed Sep. 25, 2013 to Final Office Action mailed Jul. 26, 2013", 7 pgs.

"U.S. Appl. No. 12/179,274, Response filed Oct. 21, 2011 to Final Office Action mailed Jul. 21, 2011", 11 pgs.

"U.S. Appl. No. 12/179,274, Response filed Oct. 26, 2010 to Restriction Requirement mailed Sep. 27, 2010", 9 pgs.

"U.S. Appl. No. 12/179,274, Response filed Dec. 21, 2011 to Advisory Action mailed Nov. 8, 2011", 15 pgs.

"U.S. Appl. No. 12/179,274, Response filed Dec. 21, 2012 to Final Office Action mailed Oct. 22, 2012", 13 pgs.

"U.S. Appl. No. 12/179,274, Restriction Requirement mailed Sep. 27, 2010", 5 pgs.

"Polyethylene: The Past, Present and Future", The American Academy of Orthopaedic Surgeons, Annual Meeting Scientific Program, [Online] retrieved from the internet: http://www.aaos.org/wordhtml/anmeet99/sciprog/g.htm, (1999), 20 pgs.

"Researchers Get Awards for Orthopaedic Research", The American Academy of Orthopaedic Surgeons, News Release, [Online] retrieved from the internet: <http://www.aaos.org/wordhtml/press/98press/kappa.html>, (Mar. 19, 1998), 4 pgs.

"Researchers to Get Kappa Delta Awards for Achievements", The American Academy of Orthopaedic Surgeons, Academy News, [Online] retrieved from the internet: <http://www.aaos.org/wordhtml/98news/kaooa.ht,>, (Mar. 19, 1998), 3 pgs.

Appleby, et al., "Post-Gamma Irradiation Cross-linking of Polyethylene Tape by Acetylene Treatment", Journal of Materials Science. vol. 29, (1994), 227-231.

Appleby, et al., "Property Modification of Polyethylene Tapes by Acetylene-Sensitized Gamma Irradiation", Journal of Materials Science. vol. 29, (1994), 151-156.

Bhateja, et al., "Radiation-Induced Crystallinity Changes in Polyethylene Blends", Journal of Materials Science, vol. 20, (1985), 2839-2845.

Bhateja, S, "Radiation-Induced Crystallinity Changes in Linear Polyethylene", Journal of Polymer Science: Polymer Physics Edition. vol. 21, (1983), 523-536.

Bhateja, S, "Radiation-Induced Crystallinity Changes in Linear Polyethylene: Influence of Aging", Journal of Applied Polymer Science. vol. 28, (1983), 861-872.

Bhateja, S, "Radiation-Induced Crystallinity Changes in Pressure-Crystallized Ultrahigh Molecular Weight Polyethylene", J. Macromol. Sci. Phys. B22(1), (1983), 159-168.

Bowman, J. "The Processing and Properties of y-Irradiated HOPE Granules", Intern. Polymer Processing III., (1988), 211-220.

Chen, et al., "Radiation-Induced Crosslinking: II. Effect on the Crystalline and Amorphous Densities of Polyethylene", Colloid Polym Sci. vol. 269, (1991), 469-476.

Chen, et al., "Radiation-Induced Crosslinking: III. Effect on the Crystalline and Amorphous Density Fluctuations of Polyethylene", Colloid Polym Sci. vol. 269, (1991), 353-363.

Choudhury, et al., "The Effects of Irradiation and Ageing on the Abrasive Wear Resistance of Ultra High Molecular Weight Polyethylene", Wear Elsevier Science, vol. 203-204, (1997), 335-340.

Chu, et al., "Some Structures and Properties of Very High Molecular Weight Linear Polyethylene", Bull. Inst. Chem. Res. vol. 47, No. 3, (1969), 209-221.

Crugnola, et al., "Ultrahigh Molecular Weight Polyethylene as Used in Articular Prostheses (A Molecular Weight Distribution Study)", J. of App. Polymer Science, vol. 20, (1976), 809-812.

Deng, et al., "Effects of Gamma Radiation on Tensile Properties of UHMW Polyethylene", The 20th Annual Meeting of the Society for Biomaterials, Boston, MA, (Apr. 1994), 1 pg.

Dharmastiti, et ai., "The Wear of Oriented UHMWPE Under Isotropically Rough and Scratched Counterface Test Conditions", Bio-Medical Materials and Engineering, vol. 11, (2001), 241-256.

Dijkstra, et al., "Cross-linking of Ultra-high Molecular Weight Polyethylene in the Melt by Means of Electron Beam Irradiation", Polymer, vol. 30, (May 1989), 866-873.

(56) References Cited

OTHER PUBLICATIONS

Dole, et al., "Crystallinity and Crosslinking Efficiency in the Irradiation of Polyethylene", Radiat. Phys. Chem. vol. 14, (1979), 711-720.
Du, Plessis, et al., "The Improvement of Polyethylene Prostheses Through Radiation Crosslinkino", Radiat. Phvs. Chem. vol. 9, (1977), 647-652.
Ellis, et al., "The Use of Ultrahigh Molecular Weight Polyethylene in Articular Prostheses—II. Effects of Fabrication and Gamma Sterilization on Polymer Characteristics, Coatings and Plastics Preprints", vol. 37, No. 2, American Chemical Society, (1977), 280-284.
Ellwanger, et al., "Very High Pressure Molding of Ultra High Molecular Weight Polyethylene (UHMWPE)", ANTEC, (1987), 572-574.
Gauvin, et al., "Investigation of the Radio Frequency Heating Process for UHMWPE", ANTEC, (1987), 575-578.
Greenwald, et al., "New Polys for Old: Contribution or Caveat", American Academy of Orthopaedic Surgeons, 69th Annual Meeting, (Feb. 13-17, 2002), 6 pgs.
Hamilton, et al., "Anisotropic Properties in Ultrahigh Molecular Weight Polyethylene After Cobalt-60 Irradiation", Chapter 6 from Clough, et al. "Irradiation of Polymers" ACS Symposium Series; American Chemical Society, Washington DC, (1996).
Handles, V, "Enhanced Crosslinking of Polyethylene", Radiat. Phys, Chem. vol. 14, (1979), 721-728.
Howmedica, "Material Properties, Product Quality Control, and Their Relation to UHMWPE Performance", Part Two of a Series on Ultra-High Molecular Weight Polyethylene, (1994), 1-20.
Howmedica, "Overview and Fundamentals of UHMWPE", Part One of a Series on Ultra-High Molecular Weight Polyethylene, (1994), 1-8.
Huang, H. "Mechanical Anisotropy of Self-Reinforced Polyethylene Crystallized During Continuous-Melt Extrusion", Journal of Materials Science Letters 18, (1999), 225-228.
Jahan, et al,, "Combined Chemical and Mechanical Effects on Free Radicals in UHMWPE Joints During Implantation", Journal of Biomedical Materials Research. vol. 25, (1991), 1005-1017.
Jones, et al., "Effect of γ Irradiation on the Friction and Wear of Ultrahigh Molecular weight Polyethylene", Wear, vol. 70, (1981), 77-92.
Josefsson, et al,, "Molecular Orientation of Crosslinked Polyethylene", Annual Technical Conference—Society of Plastics Enoineers, 58th vol. 2, (2000), 1725-1729.
Kang, et al., "The Radiation Chemistry of Polyethylene IX. Temperaure Coefficient of Cross-Linking and Other Effects", Journal of the American Chemical Society. vol. 89:9, (1967), 1980-1986.
Kanig, G, "Further Electron Microscope Observations on Polyethylene III. Smectic Intermediate State During Melting and Crystallization", Colloid Polym Sci. vol. 269, (1991), 1118-1125.
Kashiwabara, et al., "Radiation-Induced Oxidation of Plastics, Radiation Processing of Polymers", Chapter 11, (1992), 221-254.
Kato, el. al., "Structural Changes and Melting Behavior of γ-lrradiated Polyethylene", Japanese Journal of Applied Physics. vol. 20, No. 4., (Apr. 1981), 691-697.
Kitamaru, et al., "A Commentary Remark on the Isothermal Crystallization of a Polyethylene Gel from the Stretched Molten State", Bull. Inst. Chem. Res. vol. 46, No. 2, (1968), 97-106.
Kitamaru, et al., "Size and Orientation of Cristallites in Lightly Cross-linked Polyethylene Crystallized from the Melt Under Uniaxial Compression", Die Makromolekulare Chemie. vol. 175, (1974), 255-275.
Kitamaru, et al., "Structure and Properties of Lightly Crosslinked Crystalline Polymers Crystallized or Processed Under Molecular Orientation", Journal of Polymer Science: Macromolecular Reviews, vol. 14, (1979), 207-264.
Kitamaru, et al., "The Properties of Transparent Film Made from Linear Polyethylene by Irradiation Cross-Linking", Properties of Transparent Film. vol. 6, No. 3, (May-Jun. 1973), 337-343.
Kurth, et al., "Effects of Radiation Sterilization on UHMW-Polyethylene", ANTEC, (1987), 1193-1197.

Kurtz, et al., "Comparison of the Properties of Annealed Crosslinked (Crossfire™) and Conventional Polyethylene as Hip Bearing Materials, Bulletin—Hospital for Joint Diseases", vol. 61, Nos. 1 & 2, (2002-2003), 17-26.
Lewis, G. "Properties of Crosslinked Ultra-High-Molecular Weight Polyethylene", Biomaterials vol. 22, (2001), 371-401.
Lin, et al., "Review Structure and Plastic Deformation of Polyethylene", Journal of Materials Science. vol. 29, (1994), 294-323.
Matsubara, et al., "The Wear Properties of High-Density Polyethylene Irradiated by Gamma Rays", Wear. vol. 10, (1967), 214-222.
Meyer, B, "Recent Developments in Radiation Sterilizable Plastics", ANTEC, (1987), 1190-1192.
Minkova, et al,, "Blends of Normal High Density and Ultra-High Molecular Weight Polyethylene, γ Irradiated at a Low Dose", Colloid Polym Sci. vol. 268, (1990), 1018-1023.
Minkova, L, "DSC of γ-Irradiated Ultra-High Molecular Weight Polyethylene and High Density Polyethylene of Normal Molecular Weight", Colloid Polym Sci. vol. 266, (1988), 6-10.
Muratoglu, et al., "A Novel Method of Cross-Linking Ultra-High-Molecular Weight Polyethylene to Improve Wear, Reduce Oxidation, and Retain Mechanical Properties", The Journal of Arthroplasty. vol. 16, No. 2, (2001), 149-160.
Nakayama, et al., "Structure and Mechanical Properties of Ultra-High Molecular Weight Polyethylene Deformed Near Melting Temperature", Pure & Appl. Chem. vol. 63, No. 12, (1991), 1793-1804.
Narkis, et al., "Structure and Tensile Behavior of Irradiation—and Peroxide—Crosslinked Polyethylenes", J. Macromol. Sci.—Phys., vol. B 26, No. 1, (1987), 37-58.
Nusbaum, et al., "The Effects of Radiation Sterilization on the Properties of Ultrahigh Molecular Weight Polyethylene", Journal of Biomedical Materials Research, vol. 13, (1979), 557-76.
O'Neill, et al., "The Distribution of Oxidation Products in Irradiated Ultra-High Molecular Weight Polyethylene", Polymer Degradation and Stability. vol. 49, (1995), 239-244.
Oonishi, et al., "Comparison of Wear of UHMWPE Sliding Against Metal and Alumina in Total Hip Prostheses—Wear Test and Clinical Results", 3rd World Biomaterials Congress, Transactions, (Apr. 1988), 337 pgs.
Oonishi, et al., "Comparisons of Wear of UHMW Polyethylene Sliding Against Metal and Alumina in Total Hip Prostheses", Bioceramics. vol. 1, (1989), 272-277.
Oonishi, et al., "Effect of Cross-Linkage by Gamma Radiation in Heavy Doses to Low Wear Polyethylene in Total Hip Prostheses", Journal of Materials Science: Materials in Medicine. vol. 7, (1996), 753-763.
Oonishi, et al., "Improvement of Polyethylene by Irradiation in Artificial Joints", Radiat. Phys. Chem. vol. 39, No. 6, (1992), 495-504.
Oonishi, et al., "In Vivo and in Vitro Wear Behaviour on Weightbearing Surfaces of Polyethylene Sockets Improved by Irradiation in Total Hip Prostheses", Surface Modification Technologies V, (1992), 101-112.
Oonishi, et al., "SEM Observation on the Clinically Used Gamma-Irradiated Reinforced HDP Socket in Total Hip Replacement", Clinical Implant Materials, Advances in Bimaterials. vol. 9, (1990), 379-384.
Oonishi, et al., "The Optimum Dose of Gamma Radiation-Heavy Doses to Low Wear Polyethylene in Total Hip Prostheses", Journal of Materials Science Materials in Medicine. vol. 8, (1997), 11-18.
Oonishi, et al., "Wear Resistance of Gamma-Ray Irradiated U.H.M.W. Polyethylene Socket in Total Hip Prosthesis—Wear Test and Long Term Clinical Results", MRS Int'l. Mtg. on Adv. Mats. vol. 1, (1989), 351-356.
Oonishi, et al., "Wear Resistance of Gamma-Ray Irradiated UHMWPE Socket in Total Hip Prostheses—Wear Test and Long Term Clinical Results", 3rd World Biomaterials Congress, Transactions, (Apr. 1998), 588.
Oral, et al., "Wear Resistance and Mechanical Properties of Highly Crosslinked UHMWPE Doped with Vitamin-E", J. Arthroplasty 21 (4), (Jun. 2006), 580-591.
Patel, G. "Acceleration of Radiation-Induced Crosslinking in Polyethylene by Diacetylenes", Radiat. Phvs. Chem. vol. 14, (1979), 729-735.

(56) References Cited

OTHER PUBLICATIONS

Peacock, A, "Handbook of Polyethylene: Structures, Properties, and Applications", Chapter 8—Orientation of Polyethylene. Copyright 2000, Marcel Dekker, Inc., New York, NY.

Premnath, et al., "Gamma Sterilization of UHMWPE Articular Implants: an Analysis of the Oxidation Problem", Biomaterials. vol. 17, (1996), 1741-1753.

Prins, et al., "Biaxial Orientation of Linear Polyethylenes Using the Compressive Deformation Process", Polymer Engineering & Science. vol. 37, No. 2, (Feb. 1997), 261-269.

Rimnac, et al., "Chemical and Mechanical Degradation of UHMWPE: Report of the Development of an In Vitro Test", Journal of Applied Biomaterials. vol. 5, (1994), 17-21.

Rose, et al., "Exploratory Investigations on the Structure Dependence of the Wear Resistance of Polyethylene", Wear. vol. 77, (1982), 89-104.

Salovey, et al., "Irradiation of Ultra High Molecular Weight Polyethylene", Polymer Preprints. vol. 26, No. 1, (1985), 118-119.

Salovey, R. "On the Morphology of Crosslinking Polymers", Polymer Letters. vol. 2, (1964), 833-834.

Sandford, et al., "Shelf Life Prediction of Radiation Sterilized Medical Devices", ANTEC, (1987), 1201-1204.

Sawatari, et al., "Crosslinking Effect of Ultrahigh Molecular Weight Polyethylene-Low Molecular Weight Polyethylene Blend Films Produced by Gelation/Crystallization From Solutions", Colloid Polym Sci. vol. 269, No. 8, (1991), 795-806.

Shen, et al., "The Friction and Wear Behavior of Irradiated Very High Molecular Weight Polyethylene", Wear. vol. 30, (1974), 349-364.

Shinde, et al., "Irradiation of Ultrahigh-Molecular-Weight Polyethylene", Journal of Polymer Science: Polymer Physics Edition. vol. 23, (Feb. 1985), 1681-1689.

Silverman, "Radiation-Induced and Chemical Crosslinking: A Brief Comparison", Radiation Processing of Polymers, Chap. 2, (1992), 15-22.

Streicher, R. "Change in Properties of High Molecular Weight Polyethylenes After Ionizing Irradiation for Sterilization and Modification", Third International Conference on Radiation Processing for Plastics and Rubber, (Nov. 1987), 9 pgs.

Streicher, R. "Influence of Ionizing Irradiation in Air and Nitrogen for Sterilization of Surgical Grade Polyethylene for Implants", Radiat. Phys. Chem. vol. 31, Nos. 4-6, (1988), 693-698.

Streicher, R, "Ionizing Irradiation for Sterilization and Modification of High Molecular Weight Polyethylenes", Plastics and Rubber Processing and Applications. vol. 10, (1988), 221-229.

Streicher, R. "UHMW—Polyethylen als Werkstoff fUr artikulierende Komponenten von Gelenkendoprothesen (UHMW Polyethylene Used as a Material for the Articulating Components of Endoprostheses)", Biomed. Technik, vol. 38, (1993), 303-313.

Streicher, Robert Sulzer, "Investigation on Sterilization and Modification of High Molecular Weight Polyethylenes by Ionizing Irradiation", Reprint from beta-gamma 1/89, CH-8401, Winterthur, Switzerland, 10 pgs.

Sultan, et al., "Advances in Crosslinking Technology", Plastics, Rubber and Composites Processing and Applications 21, (1994), 65-73.

Sun, et al., "Development of an Accelerated Aging Method for Evaluation of Long-term Irradiation Effects on UHMWPE Implants", Howmedica Inc., Pfizer Hospital Products Group, (1996), 969-970.

Sun, et al., "Development of Stabilized UHMWPE Implants with Improved Oxidation Resistance Via Crosslinking", American Academy of Orthopaedic Surgeons—Scientific Exhibits, Presented at 63rd Annual MeetinQ of AAOS., (Feb. 22-26, 1996), 179-180.

Waldman, et al., "Compressive Stress Relaxation Behavior of Irradiated Ultra-High Molecular Weight Polyethylene at 37° C.", Journal of Applied Biomaterials. vol. 5, (1994), 333-338.

Wang, et al., "Melting of Ultrahigh Molecular Weight Polyethylene", Journal of Applied Polymer Science. vol. 34, (1987), 593-599.

Ward, I, "New Developments in the Production of High Modulus and High Strength Flexible Polymers", Progr Colloid Polym Sci. vol. 92, (1993), 103-110.

Ward, I, "Recent Developments in Oriented Polymers for Biomedical and Engineering Applications", Macromol. Symp. vol. 195, (2003), 293-296.

Williams, J, "Radiation Stability of Polypropylene", ANTEC, (1987), 1198-1200.

Wilson, et al,, "Proton Modification of Ultra High Molecular Weight Polyethylene to Promote Crosslinking for Enhanced Chemical and Physical Properties", Mat. Res. Soc. Symp. Proc. vol. 396, (1996), 311-316.

Wong, et al., "Molecular Deformation Processes in Gel-Spun Polyethylene Fibres", Journal of Materials Science. vol. 29, (1994), 520-526.

Yongxiang, et al., "Crosslinking of Wire and Cable Insulation Using Electron Accelerators", Radiation Processing of Polymers, Chap. 5, (1992), 71-92.

Zhao, et al., "Effect of Irradiation on Crystallinity and Mechanical Properties of Ultrahigh Molecular Weight Polyethylene", Journal of Applied Polymer Science. vol. 50, (1993), 1797-1801.

Zoepfl, et al., "Differential Scanning Calorimetry Studies of Irradiated Polyethylene: I. Melting Temperatures and Fusion Endotherms", Journal of Polymer Science: Polymer Chemistry Edition. vol. 22, (1984), 2017-2032.

Zoepfl, et al., "Differential Scanning Calorimetry Studies of Irradated Polyethylene: II. The Effect of Oxygen", Journal of Polymer Science: Polymer Chemistry Edition. vol. 22, (1984), 2033-2045.

\* cited by examiner

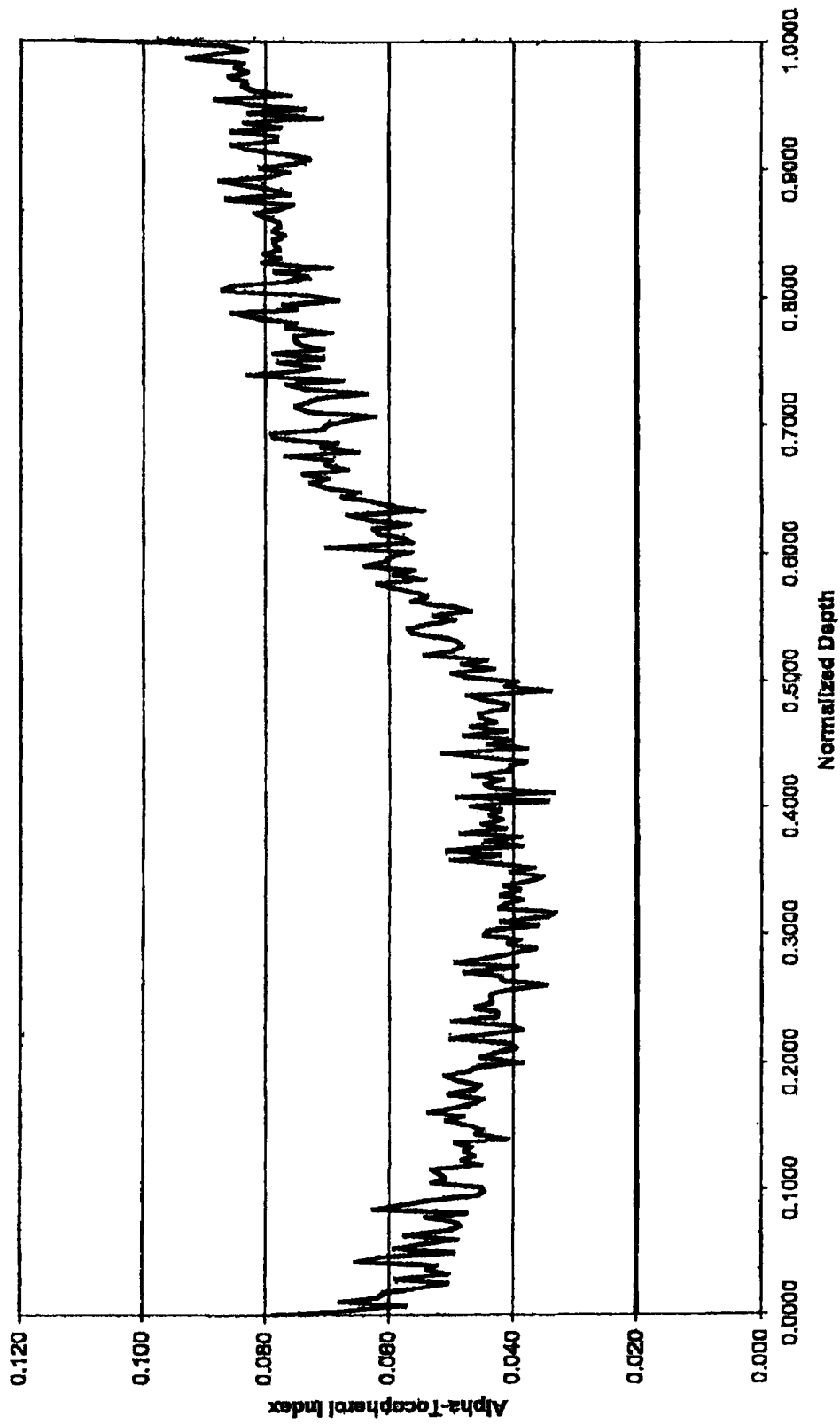

ANTIOXIDANT DOPING OF CROSSLINKED POLYMERS TO FORM NON-ELUTING BEARING COMPONENTS

CROSS-REFERENCE TO RELATED APPLICATIONS

This application is a divisional of U.S. application Ser. No. 12/179,274, filed Jul. 24, 2008, which claims the benefit of U.S. Provisional Application No. 60/952,452, filed Jul. 27, 2007, the disclosures of which are incorporated herein by reference.

INTRODUCTION

The present technology relates to antioxidant doping of crosslinked polymers. Specifically, the technology relates to processes for incorporating antioxidant materials into crosslinked polymers for use in medical implants.

Crosslinked polymers such as ultra high molecular weight polyethylene (UHMWPE) have found wide application in medical implants as bearing components. The crosslinked polymers exhibit favorable wear properties and have good bio-compatibility. In addition to good wear properties, it is also important to provide materials that resist oxidation so that the life of the material in the body can be increased.

A variety of techniques has been used to increase the oxidation stability of crosslinked materials such as UHMWPE. In some, a series of heat treatment steps is performed on the crosslinked material to decrease or eliminate the free radicals induced by the crosslinking. Recently, techniques have been developed to incorporate an antioxidant material such as vitamin E directly into the bulk material.

To incorporate an antioxidant material into a bulk polymer, a challenge is to provide a significant amount of antioxidant in the interior of the material while maintaining an acceptable non-leaching value of antioxidant on the surface. Because polymeric components suitable for making bearing components in medical implants are relatively large at 2 to 3 inches of diameter, extensive soaking times are needed, along with extended periods of annealing or homogenization to incorporate the antioxidant molecule completely into the interior of the bulk polymer. During the extensive soaking times required, it is often observed that excess antioxidant is incorporated into the UHMWPE in excess of the saturation amount. As a result, the antioxidant "sweats" or elutes from the doped bulk material.

Improved methods of doping antioxidants into crosslinked polymers in order to provide non-eluting amounts of antioxidant at the surface would be a significant advance.

SUMMARY

In various embodiments, the present technology provides polymeric materials such as UHMWPE suitable for use as bearing components in medical implants. Such implants may be used in hip replacement, knee replacements, and the like. The polymeric material is preferably crosslinked to increase its wear properties. The crosslinked polymeric material is treated by in-diffusion of antioxidant compositions that serve to or eliminate trap free radicals in the bulk material. As a result, the oxidation properties of the crosslinked material are improved. Antioxidants include, without limitation, vitamin E or tocopherols and carotenoid antioxidants, triazine antioxidants, and the like.

The present technology provides methods of making a non-eluting antioxidant doped UHMWPE, in the form of an implant bearing component. In an illustrative embodiment, the process includes the steps of: (a) machining a consolidated UHMWPE material or molding nascent UHMWPE powder to make a preform; (b) irradiating the preform with high energy irradiation such as γ-irradiation to crosslink the UHMWPE; (c) doping the crosslinked preform by exposing it to a composition comprising 10% or more by weight of an antioxidant at a temperature below the melting point of the UHMWPE; (d) removing the doped material from contact with the antioxidant composition; and then (e) annealing by heating the doped material at a temperature above 30° C. and below the melting point of the UHMWPE; followed by (f) making an implant bearing component from the doped material, wherein at least 1 mm but no more than about 15 mm of material are removed to make the component; and (g) packaging and sterilizing the bearing component or a medical implant comprising the bearing component. Specific methods include: (a) machining a consolidated UHMWPE article or molding nascent UHMWPE powder to make a preform; (b) irradiating the preform with γ-irradiation at a dose of about 5 to 20 MRad; (c) doping the irradiated preform by submerging it in vitamin E or other antioxidant at a temperature of 100° C. to 130° C. for at least one hour and preferably about 1-24 hours; (d) removing the preform from the antioxidant and heating for at least an additional hour and preferably 1-400 or greater hours at 100° C. to 130° C.; and then (e) machining the preform to form the final implant component; followed by (f) sterilizing the component by exposing it to γ-irradiation at a dose of 1-5 MRad. In some embodiments, methods include making a non-eluting antioxidant doped UHMWPE bearing component manufactured by a process comprising steps of: (a) machining a UHMWPE article or molding UHMWPE powder to make a preform; (b) irradiating the preform to a dose of 5-20 MRad; (c) doping the preform with an antioxidant; (d) machining the preform to the shape of the bearing component, while removing from 1 mm to 15 mm of material from the preform; and (f) packaging and sterilizing the bearing component.

An advantageous feature of the methods is that non-eluting antioxidant doped UHMWPE articles are produced. In particular, in various embodiments, the final components made by the methods are characterized by antioxidant index at the surface of the component that is less than the saturation limit in the component, especially as measured at body temperature, while the index throughout the component is above the detection limit. For vitamin E or α-tocopherol doped UHMWPE, the vitamin E index throughout the component is from 0.01 to 0.2, and is preferably less than or equal to 0.15. In various embodiments, the antioxidant is vitamin E, α-tocopherol, or a combination of chemical species having antioxidant properties and providing vitamin E activity. The disclosed methods provide materials useful and suitable as bearing components for implantation into the human body, for example as acetabular cups for hip implants.

BRIEF DESCRIPTION OF THE DRAWINGS

FIG. 2 is a graph of vitamin E index in an implant component.

DESCRIPTION

Figure 1A:
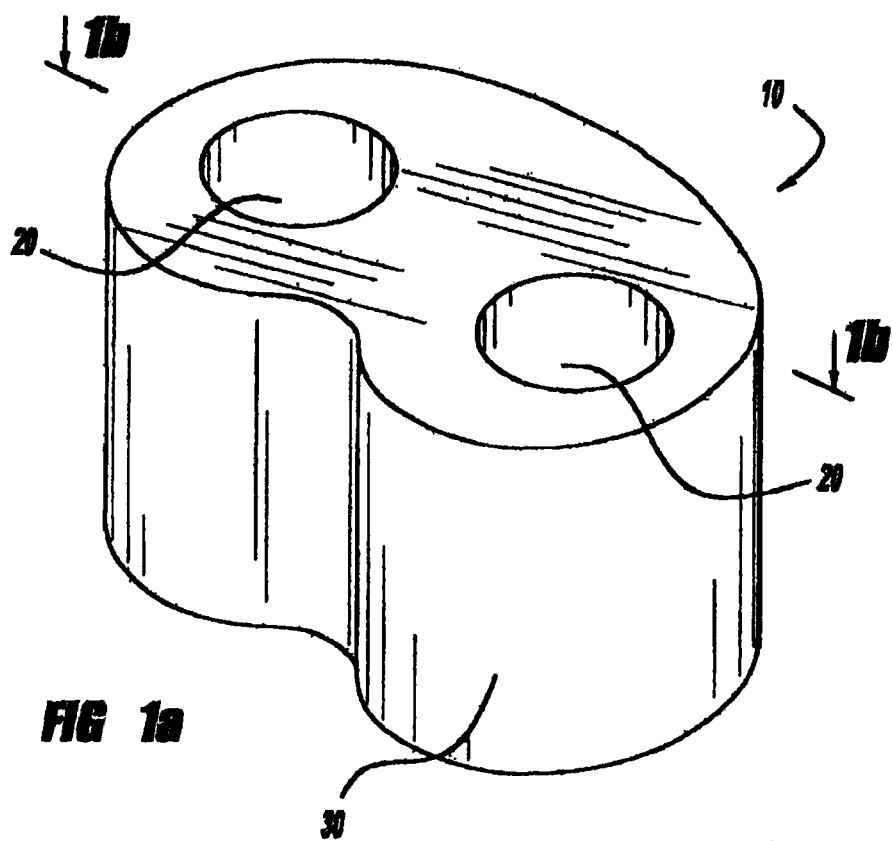
FIG. 1 shows perspective (1a) and plan (1b-1d) views of a preform and a bearing (1e) produced from the preform.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary,") used herein are intended only for general organization of topics within the present disclosure, and are not intended to limit the disclosure of the technology or any aspect thereof. In particular, subject matter disclosed in the "Introduction" may include aspects of technology within the scope of a patentable invention, and may not constitute a recitation of prior art. Subject matter disclosed in the "Summary" is not an exhaustive or complete disclosure of the entire scope of the technology or any embodiments thereof. Similarly, subpart headings in the Description are given for convenience of the reader, and are not a representation that information on the topic is to be found exclusively at the heading.

The description and specific examples, while indicating embodiments of the present technology, are intended for purposes of illustration only and are not intended to limit the scope of any invention. Moreover, recitation of multiple embodiments having stated features is not intended to exclude other embodiments having additional features, or other embodiments incorporating different combinations of the stated features. Specific Examples are provided for illustrative purposes of how to make, use and practice the compositions and methods of this technology and, unless explicitly stated otherwise, are not intended to be a representation that given embodiments of this technology have, or have not, been made or tested.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology.

The present technology provides a method of incorporating an antioxidant composition (for example, one containing vitamin E or an α-tocopherol) into a polymeric bulk material (for example, ultra high molecular eight polyethylene, or UHMWPE) by a series of doping, irradiation, heating, and machining steps. In various embodiments, the methods are characterized by a series of machining, irradiating, doping, packaging, and sterilizing steps. Methods include a final machining step after a UHMWPE preform is doped with antioxidant. In this way, bearing components and other UHMWPE articles are provided that contain significant amounts of antioxidants such as vitamin E throughout the bulk of the component or material, but which have a non-eluting value of antioxidant at the surface.

The individual steps are carried out in the order recited in the various embodiments. Various parameters of each of the steps are described below. It is intended that any of the parameters described for individual steps can be combined in processes to make suitable bearing implant components.

Polymers

Preferred polymers for use in the methods of this technology include those that are wear resistant, have chemical resistance, resist oxidation, and are compatible with physiological structures. In various embodiments, the polymers are polyesters, polymethylmethacrylate, nylons or polyamides, polycarbonates, and polyhydrocarbons such as polyethylene and polypropylene. High molecular weight and ultra high molecular weight polymers are preferred in various embodiments. Non-limiting examples include high molecular weight polyethylene, ultra high molecular weight polyethylene (UHMWPE), and ultra high molecular weight polypropylene. In various embodiments, the polymers have molecular ranges from approximate molecular weight range in the range from about 400,000 to about 10,000,000.

UHMWPE is used in joint replacements because it possesses a low co-efficient of friction, high wear resistance, and compatibility with body tissue. UHMWPE is available commercially as bar stock or blocks that have been compression molded or ram extruded. Commercial examples include the GUR series from Hoechst. A number of grades are commercially available having molecular weights in the preferred range described above.

Preparation of UHMWPE Starting Materials

Ultra high molecular weight polyethylene useful herein includes materials in flake form as are commercially available from a number of suppliers. In various embodiments, UHMWPE starting materials are produced from the powdered UHMWPE polymer by methods known in the art. In one embodiment, a preform UHMWPE is made by molding a nascent UHMWPE powder to a net shape that is close in dimension to the ultimate implant component so that the latter can be made in the subsequent machining step described below.

In another embodiment, a preform is made by machining a consolidated UHMWPE. For example, the powder can be consolidated and formed into suitable starting materials by compression molding or RAM extrusion. In one embodiment, consolidated UHMWPE is provided in the form of cylinders or rods of about 3" in diameter. Preferred processes for producing a UHMWPE starting material are described in U.S. Pat. No. 5,466,530, England et al., issued Nov. 14, 1995 and U.S. Pat. No. 5,830,396, Higgins et al., issued Nov. 3, 1998, the disclosures of which are incorporated by reference. A preform is then machined from the consolidated material.

In various embodiments, the consolidated UHMWPE starting material is first stress relieved before being subjected to the other steps described herein. Typically, stress relieving is carried out by heating the starting material to a temperature suitably high to effect stress relief but less than the melting temperature of the starting material. Typical stress relief temperature is from about 100° C. to 130° C. Stress relief is carried out for a suitable amount of time, for example from 1 to 5 hours. After stress relief, the starting material is cooled and subjected to the subsequent machining, crosslinking, doping, and final machining steps described herein.

Preform Preparation

In various embodiments, a crosslinked polymeric bulk material is further processed in a series of doping, heating, cooling, and machining steps. Before crosslinking, a preform UHMWPE is made. In one aspect, a consolidated UHMWPE starting material is optionally and preferably subjected to a first machining step to make a preform prior to subsequent irradiation and further processing. In another aspect, a preform is made by directly compressing or molding a nascent UHMWPE powder to the preform shape. Directly compressing includes forming sheets of UHMWPE in a range of thicknesses, which are then cut or otherwise shaped into preforms. In both aspects, the UHMWPE preform is given a generic shape characterized by dimensions close to those of the ultimate bearing component, but greater in each dimension by about 1 to about 15 mm. The generic shape of the preform can be compared to that of the ultimate component by considering an arbitrary line drawn through the bulk of the preform from one of its surfaces to another, defining a "dimension" of the preform. After machining of the ultimate component, a dimension is considered in the same orientation as that in the preform, again represented by a line drawn from one surface through its bulk to another surface. It is seen that the line defining the dimension in the component is shorter than the line in the preform, reflecting removal of material. Further, it is seen that, for any line in the component, material is removed at both ends of the corresponding line in the preform, and this material removal reflects shortening the line by 1 to 15 mm on both ends. The preform is thus made prior to irradiation and doping in order to permit the second machining step to be carried out with removal of only a slight amount of material on the outside of the preform in order to arrive at the ultimate shape of the bearing component. In various embodiments, the preform has a generic shape that is larger in dimensions by about 1 to about 15 mm than the ultimate bearing component so that the subsequent second machining step removes the extra 1 to 15 mm of material. In some embodiments, the amount of extra material in the generic shape is 1-10 mm or 1-4 mm. In various embodiments, the "extra" material of the preform is provided in a uniform thickness around the preform. Thus in illustrative embodiments, the preform is uniformly larger in every dimension by 1 to 15 mm than the ultimate bearing component. In such a case, the second machining step is carried out to remove the uniform shell of material around the preform to arrive at the ultimate bearing component.

Alternatively, the "extra" material of the preform can be provided in varying thicknesses, for example from 1 to 15 mm around the preform. In this case, the second machining step is carried out to remove the unevenly distributed outside shell material of the preform to arrive at the shape of the final implant.

Preferably, the preform provided after machining a consolidated UHMWPE or direct molding of a nascent UHMWPE powder has a minimum amount of extra shell material that is to be subsequently removed in a subsequent machining step. The exact dimensions and shape of the preform is selected for ease of manufacturing, keeping in consideration the desirability of removing minimal material in the subsequent machining step.

Crosslinking

The polymeric bulk material in the shape of a preform can be crosslinked by a variety of chemical and radiation methods. In various embodiments, chemical crosslinking is accomplished by combining a polymeric material with a crosslinking chemical and subjecting the mixture to temperature sufficient to cause crosslinking to occur. In various embodiments, the chemical crosslinking is accomplished by molding a polymeric material containing the crosslinking chemical. The molding temperature is the temperature at which the polymer is molded. In various embodiments, the molding temperature is at or above the melting temperature of the polymer.

If the crosslinking chemical has a long half-life at the molding temperature, it will decompose slowly, and the resulting free radicals can diffuse in the polymer to form a homogeneous crosslinked network at the molding temperature. Thus, the molding temperature is also preferably high enough to allow the flow of the polymer to occur to distribute or diffuse the crosslinking chemical and the resulting free radicals to form the homogeneous network. For UHMWPE, a preferred molding temperature is between about 130° C. and 220° C. with a molding time of about 1 to 3 hours. In a non-limiting embodiment, the molding temperature and time are 170° C. and 2 hours, respectively.

The crosslinking chemical may be any chemical that decomposes at the molding temperature to form highly reactive intermediates, such as free radicals, that react with the polymers to form a crosslinked network. Examples of free radical generating chemicals include peroxides, peresters, azo compounds, disulfides, dimethacrylates, tetrazenes, and divinylbenzene. Examples of azo compounds are: azobis-isobutyronitrile, azobis-isobutyronitrile, and dimethylazodi-isobutyrate. Examples of peresters are t-butyl peracetate and t-butyl perbenzoate.

In various embodiments the polymer is crosslinked by treating it with an organic peroxide. Suitable peroxides include 2,5-dimethyl-2,5-bis(tert-butylperoxy)-3-hexyne (Lupersol 130, Atochem Inc., Philadelphia, Pa.); 2,5-dimethyl-2,5-di-(t-butylperoxy)-hexane; t-butyl α-cumyl peroxide; di-butyl peroxide; t-butyl hydroperoxide; benzoyl peroxide; dichlorobenzoyl peroxide; dicumyl peroxide; di-tertiary butyl peroxide; 2,5-dimethyl-2,5-di(peroxy benzoate)hexyne-3; 1,3-bis(t-butyl peroxy isopropyl)benzene; lauroyl peroxide; di-t-amyl peroxide; 1,1-di-(t-butylperoxy)cyclohexane; 2,2-di-(t-butylperoxy)butane; and 2,2-di-(t-amylperoxy) propane. A preferred peroxide is 2,5-dimethyl-2,5-bis(tert-butylperoxy)-3-hexyne. The preferred peroxides have a half-life of between 2 minutes to 1 hour; and more preferably, the half-life is between 5 minutes to 50 minutes at the molding temperature. Generally, between 0.2 to 5.0 wt % of peroxide is used; more preferably, the range is between 0.5 to 3.0 wt % of peroxide; and most preferably, the range is between 0.6 to 2 wt %.

The peroxide can be dissolved in an inert solvent before being added to the polymer powder. The inert solvent preferably evaporates before the polymer is molded. Examples of such inert solvents are alcohol and acetone.

For convenience, the reaction between the polymer and the crosslinking chemical, such as peroxide, can generally be carried out at molding pressures. Generally, the reactants are incubated at molding temperature, between 1 to 3 hours, and more preferably, for about 2 hours.

The reaction mixture is preferably slowly heated to achieve the molding temperature. After the incubation period, the crosslinked polymer is preferably slowly cooled down to room temperature. For example, the polymer may be left at room temperature and allowed to cool on its own. Slow cooling allows the formation of a stable crystalline structure.

The reaction parameters for crosslinking polymers with peroxide, and the choices of peroxides, can be determined by one skilled in the art. For example, a wide variety of peroxides are available for reaction with polyolefins, and investigations of their relative efficiencies have been reported. Differences in decomposition rates are perhaps the main factor in selecting a particular peroxide for an intended application.

In various embodiments, crosslinking is accomplished by exposing a polymeric bulk material to irradiation. Non-limiting examples of irradiation for crosslinking the polymers include electron beam, x-ray, and γ-irradiation. In various embodiments, γ-irradiation is preferred because the radiation readily penetrates the bulk material. Electron beams can also be used to irradiate the bulk material. With e-beam radiation, the penetration depth depends on the energy of the electron beam, as is well known in the art.

For gamma (γ) irradiation, the polymeric bulk material is irradiated in a solid state at a dose of about 0.01 to 100 MRad (0.1 to 1000 kGy), preferably from 1 to 20 MRad, using methods known in the art, such as exposure to gamma emissions from an isotope such as $^{60}$Co. In various embodiments, γ-irradiation for a crosslinking is carried out at a dose of 1 to 20, preferably about 5 to 20 MRad. In a non-limiting embodiment, irradiation is to a dose of approximately 10 MRad.

Irradiation of the polymeric bulk material is usually accomplished in an inert atmosphere or vacuum. For example, the polymeric bulk material may be packaged in an oxygen impermeable package during the irradiation step. Inert gases, such as nitrogen, argon, and helium may also be used. When vacuum is used, the packaged material may be subjected to one or more cycles of flushing with an inert gas and applying the vacuum to eliminate oxygen from the package. Examples of package materials include metal foil pouches such as aluminum or Mylar® coating packaging foil, which are available commercially for heat sealed vacuum packaging. Irradiating the polymeric bulk material in an inert atmosphere reduces the effect of oxidation and the accompanying chain scission reactions that can occur during irradiation. Oxidation caused by oxygen present in the atmosphere present in the irradiation is generally limited to the surface of the polymeric material. In general, low levels of surface oxidation can be tolerated, as the oxidized surface can be removed during subsequent machining.

Irradiation such as γ-irradiation can be carried out on polymeric material at specialized installations possessing suitable irradiation equipment. When the irradiation is carried out at a location other than the one in which the further heating, doping, and machining operations are to be carried out, the irradiated bulk material is conveniently left in the oxygen impermeable packaging during shipment to the site for further operations.

Doping Methods

In various embodiments, an antioxidant composition is doped into the bulk material to provide antioxidant at an effective level, especially throughout the whole bulk of the components. Preferably, the methods provide a rapid method of doping to provide effective antioxidant levels. In this regard, advantage is taken of the preform shape and its close approximation to the final dimensions of the component being made. That is, since the preform is only 1-15 mm, 1-10 mm, or 1-4 mm larger in any dimension than the ultimate component, the preforms can be doped in a reasonable amount of time to provide measurable levels of antioxidant throughout the bulk of the component. Then, any surface of the doped preform that is higher in antioxidant than the saturation value can be cut off to "expose" a surface having a non-eluting value of antioxidant. In various embodiments, the shape of the preform and the time of doping and homogenizing are chosen to provide the desired level of antioxidant.

Antioxidant compositions useful herein contain one or more antioxidant compounds. Non-limiting examples of antioxidant compounds include tocopherols such as vitamin E, carotenoids, triazines, vitamin K, and others. Preferably, the antioxidant composition comprises at least about 10% of one or more antioxidant compounds. In various embodiments, the antioxidant composition is at least 50% by weight antioxidant up to an including 100%, or neat antioxidant.

As used here, the term vitamin E is used as a generic descriptor for all tocol and tocotrienol derivatives that exhibit vitamin E activity, or the biological activity of α-tocopherol. Commercially, vitamin E antioxidants are sold as vitamin E, α-tocopherol, and related compounds. The term tocol is the trivial designation for 2-methyl-2-(4,8,12-trimethyltridecyl)chroman-6-ol (compound I, $R^1$=$R^2$=$R^3$=H).

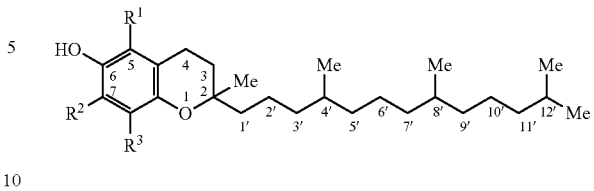

(I)

The term tocopherol is used as a generic descriptor for mono, di, and tri substituted tocols. For example, α-tocopherol is compound I where $R^1$=$R^2$=$R^3$=Me; β-tocopherol is compound I where $R^1$=$R^3$=Me and $R^2$=H. Similarly, γ-tocopherol and δ-tocopherol have other substitution patterns of methyl groups on the chroman-ol ring.

Tocotrienol is the trivial designation of 2-methyl-2-(4,8,12-trimethyltrideca-3,7,11-trienyl)chroman-6-ol.

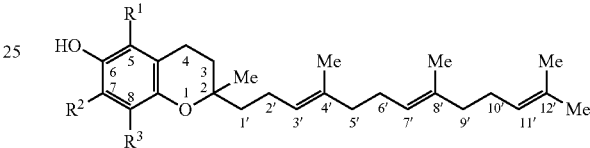

(II)

Examples of compound II include 5,7,8-trimethyltocotrienol, 5,8-dimethyltocotrienol, 7,8-dimethyltocotrienol, and 8-methyltocotrienol.

In compound I, there are asymmetric centers at positions 2, 4', and 8'. According to the synthetic or natural origin of the various tocol derivatives, the asymmetric centers take on R, S, or racemic configurations. Accordingly, a variety of optical isomers and diasteromers are possible based on the above structure. To illustrate, the naturally occurring stereoisomer of α-tocopherol has the configuration 2R, 4'R, 8'R, leading to a semi-systematic name of (2R,4'R,8'R)-α-tocopherol. The same system can be applied to the other individual stereoisomers of the tocopherols. Further information on vitamin E and its derivatives can be found in book form or on the web published by the International Union of Pure and Applied Chemistry (IUPAC). See for example, 1981 recommendations on "Nomenclature of Tocopherols and Related Compounds."

Carotenoids are a class of hydrocarbons (carotenes) and their oxygenated derivatives (xanthophylls) consisting of eight isoprenoid units joined in such a manner that the arrangement of isoprenoid units is reversed at the center of the molecule. As a result, the two central methyl groups are in a 1,6-positional relationship and the remaining nonterminal methyl groups are in a 1,5-positional relationship. The carotenoids are formally derived from an acyclic $C_{40}H_{56}$ structure having a long central chain of conjugated double bonds. The carotenoid structures are derived by hydrogenation, dehydrogenation, cyclization, or oxidation, or any combination of these processes. Specific names are based on the name carotene, which corresponds to the structure and numbering shown in compound III.

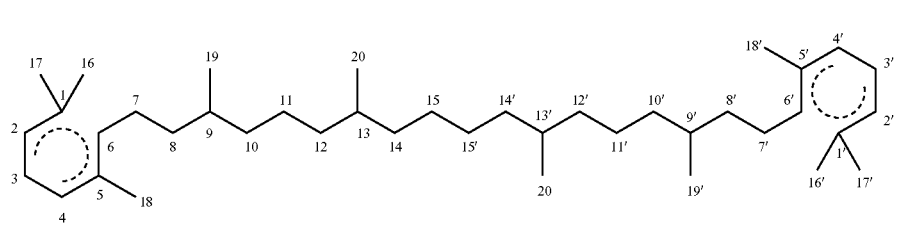

(III)

The broken lines at the two terminations represent two "double bond equivalents." Individual carotene compounds may have C$_9$ acyclic end groups with two double bonds at positions 1,2 and 5,6 (IV) or cyclic groups (such as V, VI, VII, VIII, IX, and X).

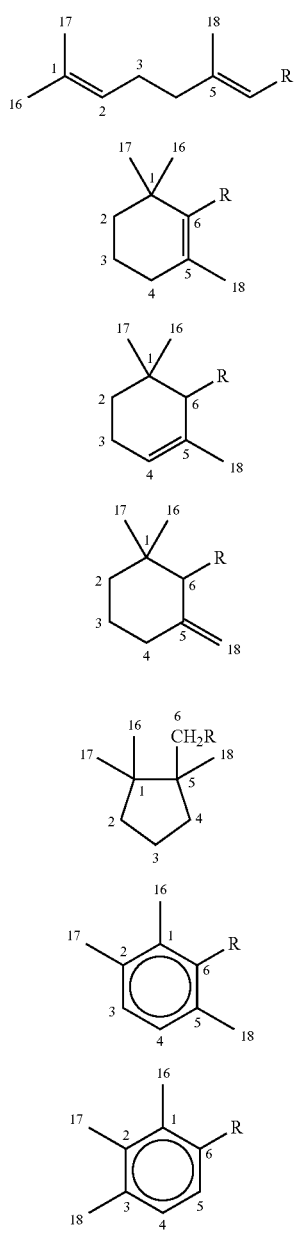

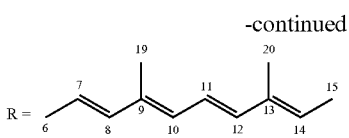

The name of a specific carotenoid hydrocarbon is constructed by adding two Greek letters as prefixes to the stem name carotene. If the end group is acyclic, the prefix is psi (ψ), corresponding to structure IV. If the end group is a cyclohexene, the prefix is beta (β) or epsilon (ε), corresponding to structure V or VI, respectively. If the end group is methylenecyclohexane, the designation is gamma (γ), corresponding to structure VII. If the end group is cyclopentane, the designation is kappa (κ), corresponding to structure VIII. If the end group is aryl, the designation is phi (Φ) or chi (χ), corresponding to structures IX and X, respectively. To illustrate, "β-carotene" is a trivial name given to a symmetrical carotenoid having beta groups (structure V) on both ends.

Elimination of a CH$_3$, CH$_2$, or CH group from a carotenoid is indicated by the prefix "nor", while fusion of the bond between two adjacent carbon atoms (other than carbon atoms 1 and 6 of a cyclic end group) with addition of one or more hydrogen atoms at each terminal group thus created is indicated by the prefix "seco". Furthermore, carotenoid hydrocarbons differing in hydrogenation level are named by use of the prefixes "hydro" and "dehydro" together with locants specifying the carbon atoms at which hydrogen atoms have been added or removed.

Xanthophylls are oxygenated derivatives of carotenoid hydrocarbons. Oxygenated derivatives include without limitation carboxylic acids, esters, aldehydes, ketones, alcohols, esters of carotenoid alcohol, and epoxies. Other compounds can be formally derived from a carotenoid hydrocarbon by the addition of elements of water (H, OH), or of alcohols (H, OR, where R is C$_{1-6}$ alkyl) to a double bond.

Carotenoids having antioxidant properties are among compounds suitable for the antioxidant compositions of the invention. Non-limiting examples of the invention include vitamin A and beta-carotene.

Other antioxidants include vitamin C (absorbic acid) and its derivatives; vitamin K; gallate esters such propyl, octyl, and dodecyl; lactic acid and its esters; tartaric acid and its salts and esters; and ortho phosphates. Further non-limiting examples include polymeric antioxidants such as members of the classes of phenols; aromatic amines; and salts and condensation products of amines or amino phenols with aldehydes, ketones, and thio compounds. Non-limiting examples include para-phenylene diamines and diaryl amines.

Antioxidant compositions preferably have at least 10% by weight of the antioxidant compound or compounds described above. In preferred embodiments, the concentration is 20% by weight or more or 50% by weight or more. In various embodiments, the antioxidant compositions are provided dissolved in suitable solvents. Solvents include organic solvents and supercritical solvents such as supercritical carbon dioxide. In other embodiments, the antioxidant compositions contain emulsifiers, especially in an aqueous system. An example is vitamin E (in various forms such as α-tocopherol), water, and suitable surfactants or emulsifiers. In a preferred embodiment, when the antioxidant compound is a liquid, the antioxidant composition consists of the neat compounds, or 100% by weight antioxidant compound.

During the doping process, the bulk material is exposed to antioxidant in a doping step followed by heat treatment or homogenization out of contact with the antioxidant. Total exposure time of the bulk material to the antioxidant is selected to achieve suitable penetration of the antioxidant. In various embodiments, total exposure time is at least several hours and preferably greater than or equal to one day (24 hours).

In various embodiments, a doping step is followed by a subsequent annealing or "homogenization" step. In one aspect, it is desirable to provide methods of achieving a suitable level of antioxidant in the interior or inner portions of the bulk material, while avoiding excess antioxidant at the outer surface. During the homogenization step, the antioxidant continues to diffuse into the interior of the bulk material. In various embodiments, the total time of annealing or homogenization is at least several hours and more preferably more than one day. For example, while there is no particular upper limit, homogenization is preferably carried out for at least an hour after doping, and typically for a period of 1 to about 400 or about 500 hours. Depending on the size of the part, the post doping heating is carried out for a period of 10 to 14 days, or for 11 to 17 days, by way of non-limiting example. In the case of vitamin E, the vitamin E index is preferably greater than or equal to about 0.01 in the center and throughout the bulk of the component, while being less than the saturation level on the outside of surface. The saturation level on the outside surface is normally taken to be the saturation level of the antioxidant in the component at body temperature, which is the approximate temperature to which the implant will be exposed when implanted. Body temperature takes on a range of values, but "normal" human body temperature is commonly referred to as 98.6° F., which converts to 37° C.

The temperature at which the exposing (doping) and annealing (homogenization) steps are carried out is preferably as high as possible but below the crystalline melting point of the material to avoid destroying the strength of the material. This is particularly useful when the material is to be used as a bearing component for a medical implant. In various embodiments, the temperature of exposure and annealing is carried out at or above 30° C., at or above 50° C., at or above 80° C., at or above 100° C., and at or above 120° C. Preferably, the temperature is below the melting point of the bulk polymer. Preferred temperatures, especially for the case of UHMWPE, include less than or about 135° C. and less than or about 130° C. In a preferred embodiment, UHMWPE is exposed and annealed (homogenized) at a temperature of about 130° C.

The doping and homogenization steps can be repeated as desired to achieve suitable dispersion of the antioxidant through the bulk preform. In various embodiments, breaking up the time of exposure to antioxidant and the time of homogenization into two or more periods provides greater diffusion of the antioxidant into the interior of the bulk material than the same amount of time of exposure in one dose. At the same time, the method tends to avoid an accumulation of antioxidant on the surface of the bulk material, which could lead to undesirable exudation or "sweating" of the bulk material, as excess antioxidant rises to the surface and escapes from the bulk. Furthermore, without limiting the scope, function or utility of the present technology, it is believed that the sequential doping method provide additional "driving force" for the diffusion of antioxidant into the interior of the bulk material. The driving force is proportional to the concentration difference or gradient of the antioxidant such as α-tocopherol on the surface and inside the bulk of the polymeric material. As the antioxidant diffuses into the bulk, the driving force is reduced. In various embodiments, the methods of the invention counteract the reduced driving force by recharging it periodically with sequential doping of the antioxidant.

In various embodiments, the sequence of steps constituting a doping/removing/heating cycle is carried out 2, 3, 4, or more times as desired to provide the desired level of doping of antioxidant. Preferably, the total time of exposure of the polymeric bulk material to the antioxidant during the plurality of doping cycles is at least several hours, preferably greater than one day and preferably greater than two days, up to 3 weeks, 2 weeks, or one week when held for example at about 130° C. The total time of annealing or homogenization when out of contact with the antioxidant composition is preferably at least several hours over the plurality of cycles. Preferably, the annealing time is greater than one day and preferably greater than two days, up to one week, two weeks, or three weeks of total annealing time during the cycles. During the annealing steps when out of contact, the antioxidant further diffuses into the interior of the bulk material.

In a particular embodiment, the present technology provides a method of making an oxidation resistant UHMWPE by exposing a polymeric material to an antioxidant composition comprising vitamin E. The method involves exposing a bulk crosslinked UHMWPE to a composition comprising vitamin E at a temperature below the crystalline melting point of the UHMWPE. Thereafter, the bulk UHMWPE is removed from exposure to the vitamin E composition and is annealed by heating it to a temperature greater than 30° C. and below the melting point. The exposing and annealing steps can be repeated at least once, preferably until the vitamin E index measured throughout the preform is at least 0.01 while the vitamin E index on the outside surface of the bar preferably remains less than the saturation value. The vitamin E index throughout the preform preferably is in the range of 0.01 to 0.2, or 0.01 to 0.15, or 0.01 to 0.10. In this and other embodiments, it is understood that removing the UHMWPE from exposure to the vitamin E composition encompasses either removing the bar physically from the composition or removing the composition while leaving the bar in place. Combinations of the two methods may also be used. It is further understood that exposing the bulk material to the antioxidant composition can involve either plunging the bulk material into the composition or pouring the composition onto the bar to cover it. As before, combinations of the two may also be used.

Machining to the Final Shape of the Implant Component

A machining step is carried out to produce a UHMWPE material in the shape of the ultimate bearing component. As noted, the step is used to remove a fairly small amount of material, illustratively from 1 to 15 mm, 1 to 10 mm, or 1 to 4 mm from the preform that was crosslinked, and then doped with antioxidant. Advantageously, the dimensions of the preform can be selected so that, depending on demand, a number of different implant components or sizes of implant components can be machined from the preform. Thus for example, it is possible to make and stockpile a supply of preforms, and produce implant components as needed in the sizes required. The machining step removes an outer surface or layer of the preform. This may provide the further advantage of removing an eluting outer layer of the preform that might have been produced during the doping and homogenizing steps.

Non-limiting examples of implant components include tibia bearings, acetabular linings, glenoid components of an artificial shoulder, and spinal components such as those used for disk replacement or in a motion preservation system.

Products of the Methods

In various embodiments, the methods provide bulk materials especially in the form of a medical implant bearing components having significant levels of antioxidants throughout the interior of the bulk material. In a preferred embodiment, the implants have a level of antioxidant that is below the saturation level at which sweating or eluting of antioxidant would be observed. When the antioxidant is based on the tocopherol molecule (vitamin E) the vitamin E index in the interior of the components is at least 0.01, and is preferably greater than 0.02, while the vitamin E index on the exterior (i.e. at points close to or on the surface) is preferably less than or equal to 0.2.

Vitamin E index is measured from infrared absorbent experiments carried out on thin sections of doped material. Absorbance due to vitamin E between 1226 and 1275 $cm^{-1}$ is integrated and compared to a reference absorbance peak located between about 1850 and 1985 $cm^{-1}$. The ratio of the two peaks is the vitamin E index. The vitamin E index has a detectable level of about 0.008 or 0.01.

Experimentally, suitable vitamin E doping can be determined by measuring the index at a point in the interior of the preform or of the component that is the farthest from a surface of the respective solid. If the index at a point farthest from the surface is above a minimum value, then other points in the component closer to the surface are expected to have at least that index or higher. Similarly, the measured index on the surface is likely to be a maximum, so that no interior point of the component will have an index higher than that measured on the surface. These considerations follow from the fact that the antioxidant is diffused into a bulk preform from outside. During doping, the duration of which is dependent on the size of the preform, the antioxidant diffuses from the exterior surface into the interior. When the interior of the preform reaches a vitamin E index of at least 0.01 and preferably at least 0.02, the preform is ready for the subsequent steps described herein. In preferred embodiments, the exterior vitamin E index of the finished part is lower than that which causes the vitamin E in the component to sweat or elute from the surface, even though the preform from which the part is made exhibits a surface or exterior index that causes it to noticeably sweat or elute.

In the case of γ-crosslinked UHMWPE, the doped polymeric bulk material contains a measurable level of free radicals resulting from the γ-irradiation and crosslinking. Nevertheless, without limiting the scope, function or utility of the present technology, it is believed that the free radicals are associated in the bulk material with antioxidant molecules. As a result, the doped bulk material is resistant to oxidation, exhibiting an oxidation index increase of less than 0.5 when exposed to oxygen at 70° C. for four weeks. Preferably, the oxidation index increases less than 0.2, or less than 0.1. In preferred embodiments, the oxidation index essentially does not change during exposure to oxygen at elevated temperatures for times up to four weeks.

In general, the free radical concentration in the polymer changes as the various process steps are carried out. The consolidated UHMWPE starting material and the nascent UHMWPE powder contain essentially no free radicals. The unirradiated preforms likewise have essentially no detectable free radicals. On crosslinking, the free radical concentration grows to a significant level, which is slightly reduced when the irradiated preform is doped with antioxidant. The level of detectable free radicals is further significantly reduced during the post doping heat treatment, annealing, or homogenizing step. The final machining step has little effect on free radicals, while the final irradiation sterilization increases free radicals slightly. Non-irradiative sterilization has no effect on free radicals. But throughout, the free radicals are not reduced to non-detectable levels at any time after the irradiation. This is in contrast to crosslinked materials that have been heated or even melted to recombine free radicals and reduce their concentration. But despite the relatively higher concentration of free radicals, antioxidant-doped crosslinked polymers of the invention maintain a high resistance to oxidation, which, without limiting the scope, function or utility of the present technology, is believed to be attributable to a sequestration of the free radicals in close association with the antioxidant compounds.

Oxidation index is calculated by measuring the infrared absorbance of the carbonyl band at about 1740 $cm^{-1}$ and comparing it to the methylene vibration at about 1370 $cm^{-1}$. The methylene vibration absorbents corrects for the thickness of the test sample. In a preferred embodiment, oxidation index measurement and calculations are based on ASTM F 2102-01. Oxidation peak area is the integrated area below the carbonyl peak between 1650 and 1850 $cm^{-1}$. The normalization peak area is the integrated area below the methylene stretch between 1330 and 1396 $cm^{-1}$. Oxidation index is calculated by dividing the oxidation peak area by the normalization peak area.

In various embodiments, implant bearing components are manufactured from polymeric starting materials using the methods described herein. Non-limiting examples of bearing components include those in hip joints, knee joints, ankle joints, elbow joints, shoulder joints, spine, temporo-mandibular joints, and finger joints. In hip joints, for example, the methods can be used to make the acetabular cup or the insert or liner of the cup. In the knee joints, the compositions can be made used to make the tibial plateau, the patellar button, and trunnion or other bearing components depending on the design of the joints. In the ankle joint, the compositions can be used to make the talar surface and other bearing components. In the elbow joint, the compositions can be used to make the radio-numeral or ulno-humeral joint and other bearing components. In the shoulder joint, the compositions can be used to make the glenero-humeral articulation and other bearing components. In the spine, intervertebral disc replacements and facet joint replacements may be made from the compositions.

The methods described herein provide additional benefits to the manufacturing process. When doping is carried out on a finished component, growth and shrinkage of the UHMWPE observed upon addition of antioxidant can cause the geometry to change significantly. On the other hand, machining the final component from a near net shape preform as described herein produces a product that is dimensionally accurate and dimensionally stable. The machining step thus eliminates a variable and makes the process more predictable.

The materials, methods and devices of the present technology are further exemplified by the following non-limiting examples.

EXAMPLES

Example 1

Figure 1B:
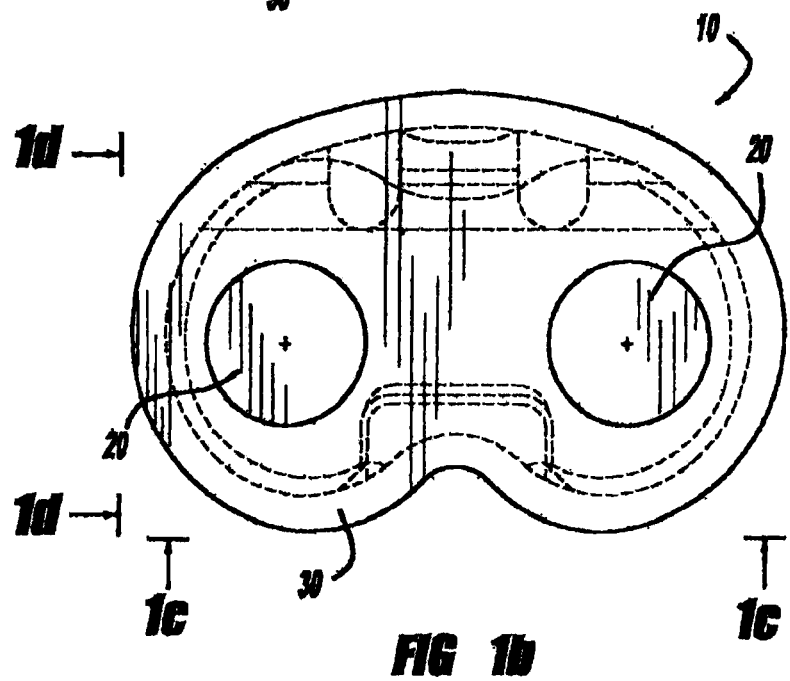
Figure 1C:
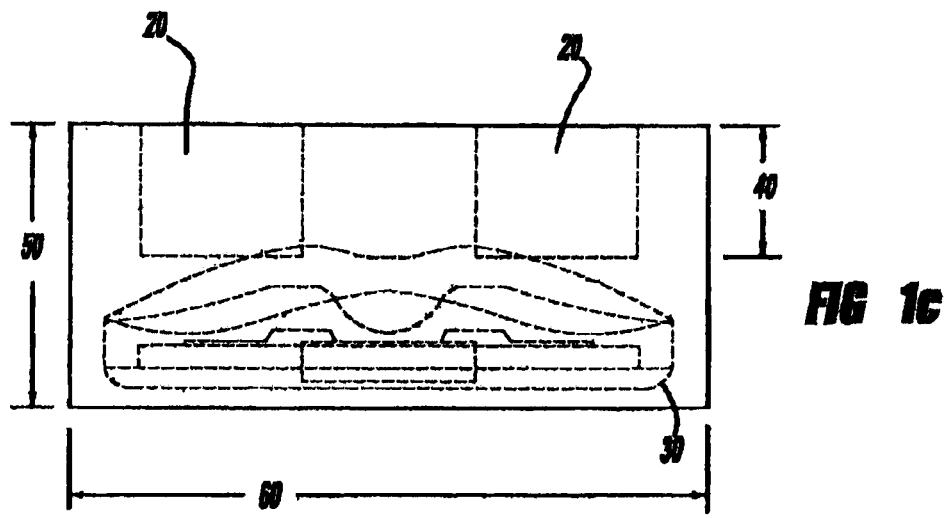
Figure 1D:
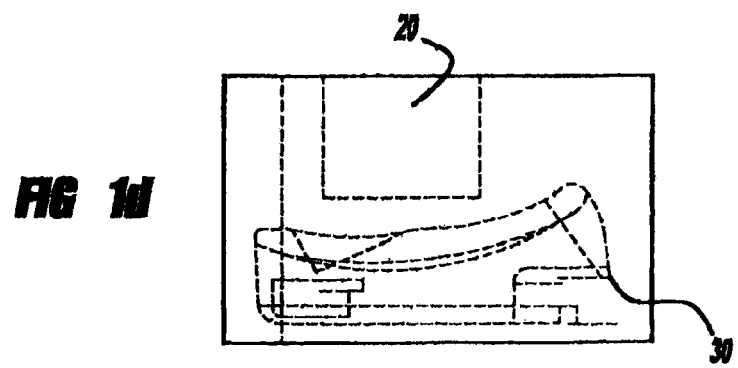
Figure 1E:
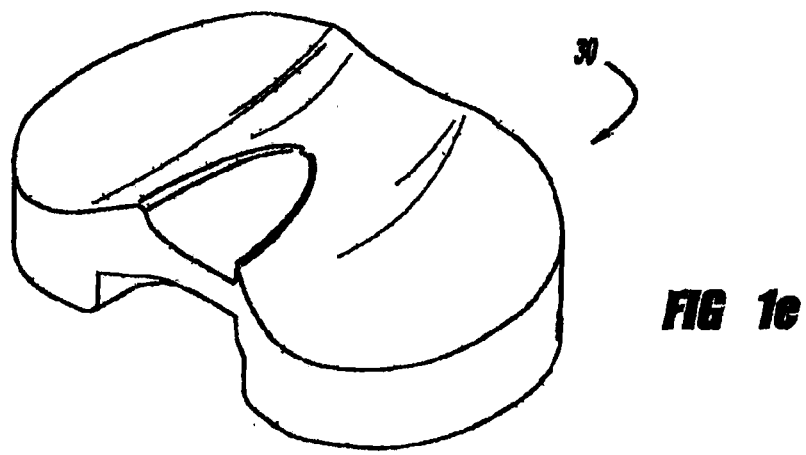

FIG. 1a shows a perspective view of a tibial preform 10 characterized by an overall kidney shape and containing two non-through holes 20. FIG. 1b shows a plan view of the top of the preform 10. Hidden lines indicate schematically the rough position of a tibial bearing 30 to be machined out of the preform 10. FIG. 1c is a plan view showing the depth 40 of the non-through holes 20 and the height 50 and length 60 of the preform 10. FIG. 1d is another side plan view showing the non-through holes 20 and the hidden lines of the tibial bearing 30. FIG. 1e is a perspective of the tibial bearing 30 prepared by machining the preform.

The views of FIG. 1 illustrate the preform in relation to the implant component machined from it. A line from the surface 70 of the preform to the component 30, when drawn in its shortest length, will be, in various embodiments, 1-15 mm, 1-10 mm, or 1-4 mm in length. Put another way, the outer surface of the component is within 15 mm of the outer surface of the preform.

Example 2

Preparing an implant component involves the following steps:

An acetabular preform is machined from UHMWPE barstock. A typical preform is shown in FIG. 1a.

The preform is then cleaned in isopropyl alcohol, placed in a barrier film bag, the bag is placed in a chamber which evacuates the air, purges with argon, evacuates the argon and then seals the package.

The preforms are then boxed in a double layer and sent for gamma irradiation to a dose of 100±10 kGy.

When the preforms return, they are removed from the barrier film packaging and doped in vitamin E (dl-α-tocopherol) for 8 hours at 122° C.

At the end of the doping cycle, the excess vitamin E is cleaned from the surface.

The preforms are then placed in an inert gas oven and heated to 130° C. and the temperature is held for 264 hours. At the end of the 264 hours, the oven is cooled to room temperature over 6 hours.

FTIR testing is used to quantify the amount of vitamin E in the polyethylene where the diffusion distance is a maximum. The minimum vitamin E index is 0.02.

The preform is then machined into a liner by removing a minimum of 1.5 mm of material from all surfaces of the pre-form.

The liners are then laser etched with the lot number, cleaned in isopropyl alcohol, barrier film packaged with an argon purge, blister packed, and boxed and labeled.

The components are then sent for gamma sterilization with a dose of 25-40 kGy.

A typical vitamin E profile taken after this step is shown in FIG. 2. For example, the vitamin E index in an acetabular cup is measured in a line from the inner diameter to the outer diameter, according to the procedure of Example 3.

Example 3

Equipment for measuring vitamin E or other antioxidant index includes an FTIR spectrometer, a microtome capable of 200 μm thick slices, an it microscope with automated stage, and computer software capable of collecting spectra across a sample and creating a profile of peak area ratios for two specific peaks. Measuring the index of a part such as an implant component or a preform involves the following steps:
1. Cut the part such that the area farthest from all surfaces is exposed. This will be the area with the lowest concentration of vitamin E.
2. Use the microtome to make a 200 μm thick slice of the preform. The cut direction is perpendicular to the measurement direction. (The measurement direction is generally the shortest distance between two surfaces that passes through the area with the lowest vitamin E concentration.)
3. Secure the sample to a slotted metal slide with magnets such that the measurement direction is parallel to the slot.
4. Place the slide in the microscope such that the measuring direction is parallel to the X-axis of the microscope.
5. Using the mapping tool on the FTIR software, create a mapping line from one surface of the sample to the other along the measurement direction.
6. Collect spectra at 200 μm intervals along the mapping line.
7. Use the software to create a profile along the mapping line of the ratio of the peak area of the vitamin E peak (1245-1275) to the peak area of the polyethylene peak (1850 to 1985). The resulting profile shows the vitamin E index through the area of the polyethylene that is the farthest distance from all surfaces.

The examples and other embodiments described herein are exemplary and not intended to be limiting in describing the full scope of devices and methods of this technology. Equivalent changes, modifications and variations of specific embodiments, materials, devices and methods may be made within the scope of the present technology, with substantially similar results.

We claim:

1. A non-eluting antioxidant doped UHMWPE bearing component manufactured by a process comprising steps of:
    (a) providing a UHMWPE preform;
    (b) irradiating the preform at a dose of 5 to 20 MRad of gamma irradiation;
    (c) after the irradiating, doping the preform by exposure to an antioxidant composition comprising α-tocopherol at a temperature greater than 30° C. and below the crystalline melting point of the UHMWPE preform, and then removing the doped UHMWPE preform from exposure to the antioxidant composition;
    (d) annealing the doped preform at a temperature greater than 30° C. and below the melting point of the doped preform;
    (e) machining the preform to the shape of the bearing component, wherein from 1 to 15 mm of material is removed from the preform to make the component; and
    (f) packaging and sterilizing the bearing component, wherein the vitamin E index throughout the bearing component is 0.01 or greater, and 0.2 or less, wherein the vitamin E index is determined from a Fourier transform infrared spectrum of the bearing component as the ratio of the area of the α-tocopherol peak at 1245-1275 cm$^{-1}$ to the area of the polyethylene peak at 1850-1985 cm$^{-1}$.

2. A bearing component according to claim 1, made by irradiating the preform to a dose of approximately 10 MRad.

3. A bearing component according to claim 1, wherein the vitamin E index throughout the component is 0.15 or less.

4. A bearing component according to claim 1, characterized by having a vitamin E index at the surface of the component that is less than the saturation limit of vitamin E in the component at body temperature.

5. A medical implant bearing component made of irradiation-crosslinked UHMWPE comprising post-irradiative-crosslinking added vitamin E, wherein the vitamin E index of the bearing component is at least 0.01 throughout its volume and the vitamin E index at the outer surface of the bearing component is less than or equal to 0.2, wherein the vitamin E index is determined from a Fourier transform infrared spectrum of the bearing component as the ratio of the area of the α-tocopherol peak at 1245-1275 cm$^{-1}$ to the area of the polyethylene peak at 1850-1985 cm$^{-1}$.

6. The bearing component according to claim 5, wherein the vitamin E index of the bearing component is at least 0.02 throughout its volume.

7. The bearing component according to claim 5, comprising a detectable level of free radicals greater than zero.

8. The bearing component according to claim 5, wherein the oxidation index of the bearing component changes by less than 0.1 when exposed to oxygen at 70° C. for 4 weeks.

9. The bearing component according to claim 5, wherein the bearing component is for a hip joint.

10. The bearing component according to claim 9, wherein the bearing component is an acetabular cup.

11. The bearing component according to claim 5, wherein the bearing component is for a knee joint.

12. The bearing component according to claim 11, wherein the bearing component is a tibial plateau.

13. The bearing component according to claim 5, wherein the bearing component is for an ankle joint.

14. The bearing component according to claim 5, wherein the bearing component is for an elbow joint.

15. The bearing component according to claim 5, wherein the bearing component is for a shoulder joint.

16. The implanting bearing component according to claim 5, wherein the bearing component is for a spine implant.

17. The bearing component according to claim 5, wherein the bearing component is for a temporomandibular joint.

18. The bearing component according to claim 5, wherein the bearing component is for a finger joint.

* * * * *